United States Patent [19]
Netta

[11] Patent Number: 5,830,159
[45] Date of Patent: Nov. 3, 1998

[54] FLAT TELL MAMMOGRAM

[76] Inventor: Henrietta Netta, 246 Coal St., Wilkes-Barre, Pa. 18702

[21] Appl. No.: 878,644

[22] Filed: Jun. 19, 1997

[51] Int. Cl.[6] .................................................. A61B 5/103
[52] U.S. Cl. .......................................... 600/587; 600/549
[58] Field of Search ..................................... 600/549, 587

[56] References Cited

U.S. PATENT DOCUMENTS

| | | | |
|---|---|---|---|
| 4,055,160 | 10/1977 | Simpson et al. | 600/549 |
| 5,301,681 | 4/1994 | DeBan et al. | 128/736 |
| 5,546,955 | 8/1996 | Wilk | 128/736 |

*Primary Examiner*—Max Hindenburg
*Assistant Examiner*—Pamela Wingood

[57] ABSTRACT

A breast anomaly detection system is provided including a brassiere with a pair of cups. Further provided is a pair of temperature and pressure sensors each coupled to an associated cup of the brassiere. Each temperature and pressure sensor is adapted to emit a temperature and pressure signal representative of a current temperature and pressure of the breast located within the associated cup, respectively. Further included is control circuitry adapted for comparing the temperature and pressure signals with stored values and providing an alert upon the temperature or pressure signals differing from the stored values.

7 Claims, 1 Drawing Sheet

FLAT TELL MAMMOGRAM

BACKGROUND OF THE INVENTION

1. Field of the Invention

The present invention relates to mammogram apparatuses and more particularly pertains to a new FLAT TELL MAMMOGRAM for detecting the presence of a tumor or infection within a breast of a user.

2. Description of the Prior Art

The use of mammogram apparatuses is known in the prior art. More specifically, mammogram apparatuses heretofore devised and utilized are known to consist basically of familiar, expected and obvious structural configurations, notwithstanding the myriad of designs encompassed by the crowded prior art which have been developed for the fulfillment of countless objectives and requirements.

Known prior art mammogram apparatuses include U. S. Pat. No. 4,759,045; U.S. Pat. No. 4,090,084; U.S. Pat. Des. 334,980; U.S. Pat. No. 5,365,429; U.S. Pat. No. 5,339,349; and U.S. Pat. No. 5,283,823.

In these respects, the FLAT TELL MAMMOGRAM according to the present invention substantially departs from the conventional concepts and designs of the prior art, and in so doing provides an apparatus primarily developed for the purpose of detecting the presence of a tumor or infection within a breast of a user.

SUMMARY OF THE INVENTION

In view of the foregoing disadvantages inherent in the known types of mammogram apparatuses now present in the prior art, the present invention provides a new FLAT TELL MAMMOGRAM construction wherein the same can be utilized for detecting the presence of a tumor or infection within a breast of a user.

The general purpose of the present invention, which will be described subsequently in greater detail, is to provide a new FLAT TELL MAMMOGRAM apparatus and method which has many of the advantages of the mammogram apparatuses mentioned heretofore and many novel features that result in a new FLAT TELL MAMMOGRAM which is not anticipated, rendered obvious, suggested, or even implied by any of the prior art mammogram apparatuses, either alone or in any combination thereof.

To attain this, the present invention generally comprises a brassiere with a pair of cups. As shown in FIG. 1, each cup has a rear opening with an arcuate upper edge, an arcuate outer side edge, a linear bottom edge, and an arcuate inner side edge. The inner side edges of the rear openings of the cups are stitchedly coupled by way of a generally triangular piece of inelastic fabric. The brassiere further includes a back strap with ends coupled to the outer side edges of the rear openings of the cups. Associated therewith is a pair of shoulder straps coupled between the back strap and the upper edges of the rear openings of the cups. By this structure, a female user may wear the brassiere such that each breast thereof resides within an associated one of the cups. Next provided is a pair of temperature sensors. Each of such temperature sensors is coupled to an associated cup of the brassiere adjacent an interconnection of the upper edge and outer side edge thereof. In use, each temperature sensor is adapted to emit a temperature signal representative of a current temperature of the breast located within the associated cup. Further included is a pair of strain gauges each coupled to an associated cup of the brassiere. Such coupling is preferably afforded adjacent a central extent of the bottom edge thereof. In operation, each strain gauge is adapted to emit a pressure signal representative of a current pressure that is exerted by the breast on the associated cup. With reference now to FIG. 2, it can be seen that a multiplexer is included and connected to each of the temperature sensors and strain gauges. The multiplexer is adapted for allowing the transmission from an output thereof the temperature signals and pressure signals one at a time upon receipt of an activation signal. Connected to the output of the multiplexer is an analog to digital converter for transforming the temperature signals and pressure signals from analog form to digital form. Further included is memory means adapted to store and transmit a pair of temperature signals and pressure signals in digital form. Connected between the multiplexer, analog to digital converter, and memory means is control circuitry. In use, the control circuitry is adapted for transmitting a continuous sequence of activation signals to the multiplexer. Upon the receipt of each signal from the analog to digital converter, the control circuitry compares the digital temperature signals and pressure signals received from the analog to digital converter with the temperature signals and pressure signals received from the memory means, respectively. In addition, the control circuitry is further adapted to transmit an alert signal upon at least one of the digital temperature signals and pressure signals received from the analog to digital converter differing from the respective temperature signals and pressure signals received from the memory means, respectively, by a predetermined amount. Finally, for printing an alert upon the receipt of the alert signal, a printer is connected to the control circuitry.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature an essence of the technical disclosure of the application. The abstract is neither intended to define the invention of the application, which is measured by the claims, nor is it intended to be limiting as to the scope of the invention in any way.

It is therefore an object of the present invention to provide a new FLAT TELL MAMMOGRAM apparatus and method which has many of the advantages of the mammogram apparatuses mentioned heretofore and many novel features that result in a new FLAT TELL MAMMOGRAM which is not anticipated, rendered obvious, suggested, or even implied by any of the prior art mammogram apparatuses, either alone or in any combination thereof.

It is another object of the present invention to provide a new FLAT TELL MAMMOGRAM which may be easily and efficiently manufactured and marketed.

It is a further object of the present invention to provide a new FLAT TELL MAMMOGRAM which is of a durable and reliable construction.

An even further object of the present invention is to provide a new FLAT TELL MAMMOGRAM which is susceptible of a low cost of manufacture with regard to both materials and labor, and which accordingly is then susceptible of low prices of sale to the consuming public, thereby making such FLAT TELL MAMMOGRAM economically available to the buying public.

Still yet another object of the present invention is to provide a new FLAT TELL MAMMOGRAM which provides in the apparatuses and methods of the prior art some of the advantages thereof, while simultaneously overcoming some of the disadvantages normally associated therewith.

Still another object of the present invention is to provide a new FLAT TELL MAMMOGRAM for detecting the presence of a tumor or infection within a breast of a user.

Even still another object of the present invention is to provide a new FLAT TELL MAMMOGRAM that comprises a brassiere including a pair of cups. Further provided is a pair of temperature and pressure sensors each coupled to an associated cup of the brassiere. Each temperature and pressure sensor is adapted to emit a temperature and pressure signal representative of a current temperature and pressure of the breast located within the associated cup, respectively. Further included is control circuitry adapted for comparing the temperature and pressure signals with stored values and providing an alert upon the temperature or pressure signals differing from the stored values.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
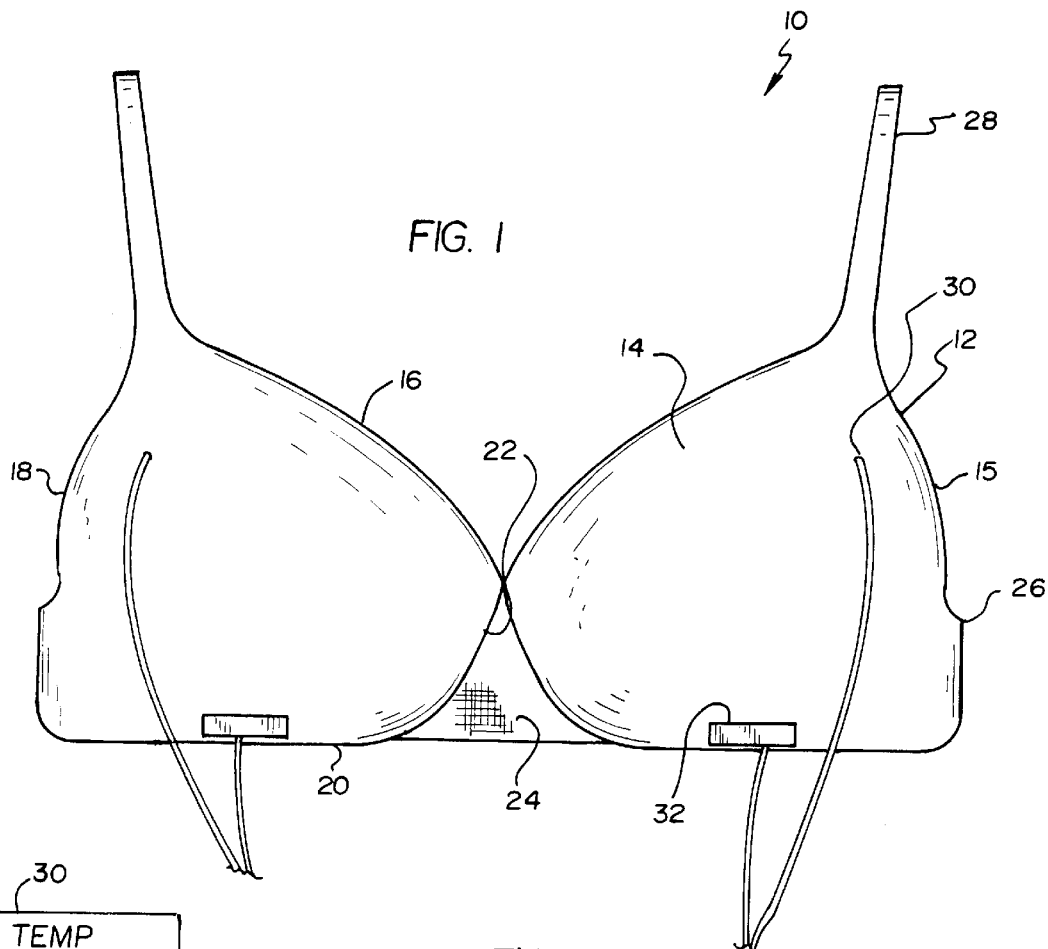
FIG. 1 is a front view of a new FLAT TELL MAMMOGRAM according to the present invention.

With reference now to the drawings, a new FLAT TELL MAMMOGRAM embodying the principles and concepts of the present invention and generally designated by the reference numeral 10 will be described.

More specifically, it will be noted that the system 10 of the present invention includes a brassiere 12 with a pair of cups 14. As shown in FIG. 1, each cup has a rear opening 15 with an arcuate upper edge 16, an arcuate outer side edge 18, a linear bottom edge 20, and an arcuate inner side edge 22. The inner side edges of the rear openings of the cups are stitchedly coupled by way of a generally triangular piece of inelastic fabric 24. The brassiere further includes a back strap 26 with ends coupled to the outer side edges of the rear openings of the cups. Associated therewith is a pair of shoulder straps 28 coupled between the back strap and the upper edges of the rear openings of the cups. By this structure, a female user may wear the brassiere such that each breast thereof resides within an associated one of the cups.

Next provided is a pair of temperature sensors 30. Each of such temperature sensors is coupled to an associated cup of the brassiere adjacent an interconnection of the upper edge and outer side edge thereof. In use, each temperature sensor is adapted to emit a temperature signal representative of a current temperature of the breast located within the associated cup.

Further included is a pair of strain gauges 32 each coupled to an associated cup of the brassiere. Such coupling is preferably afforded adjacent a central extent of the bottom edge thereof. In operation, each strain gauge is adapted to emit a pressure signal representative of a current pressure that is exerted by the breast on the associated cup. Such pressure is a direct function of the size of the breast. It should be noted that more than one temperature and pressure sensor may be coupled to each cup of the brassiere for providing a more accurate indication of the temperature and size of various areas of the breast.

Figure 2:
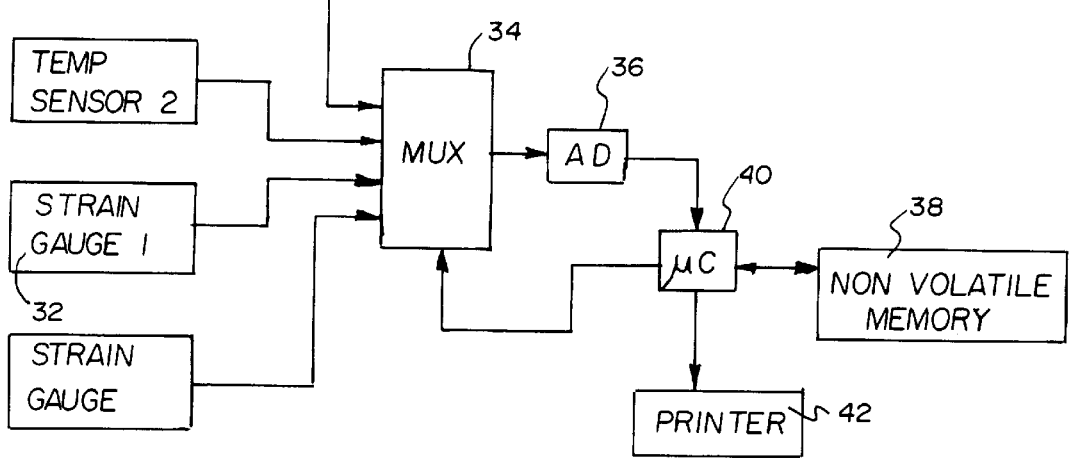
FIG. 2 is a schematic diagram of the electrical components of the present invention.

With reference now to FIG. 2, it can be seen that a multiplexer 34 is included and connected to each of the temperature sensors and strain gauges. The multiplexer is adapted for allowing the transmission from an output thereof the temperature signals and pressure signals one at a time upon receipt of an activation signal. Connected to the output of the multiplexer is an analog to digital converter 36 for transforming the temperature signals and pressure signals from analog form to digital form. Further included is memory means 38 adapted to store and transmit a pair of temperature signals and pressure signals in digital form. For reasons that will become apparent later, the memory means is preferably of the non-volatile type for storing the temperature and pressure signals over extended periods of time.

Connected between the multiplexer, analog to digital converter, and memory means is control circuitry 40. In use, the control circuitry is adapted for transmitting a continuous sequence of activation signals to the multiplexer at a predetermined clock rate. Upon the receipt of each signal from the analog to digital converter, the control circuitry compares the digital temperature signals and pressure signals received from the analog to digital converter with the pair of temperature signals and pressure signals received from the memory means, respectively.

In addition, the control circuitry is further adapted to transmit an alert signal upon at least one of the digital temperature signals and pressure signals received from the analog to digital converter differing from the respective temperature signals and pressure signals received from the memory means, respectively, by a predetermined amount. While not shown, it is preferred that the control circuitry is equipped with a control switch such that a user may selectively actuate the same only when the user is remaining still and has completely exhaled. Further, it is preferred that the control circuitry be equipped with a reset switch for recording in the memory means a currently measured temperature and pressure signal for each sensor. It should be noted that the multiplexer is adapted to begin transmitting the signals in the same order upon every receipt of a new sequence of activation signals. This allows the control circuitry to ensure that the sensors are compared to the proper signals within the memory means.

Finally, for printing an alert upon the receipt of the alert signal, a printer 42 is connected to the control circuitry. In the preferred embodiment, the alert consists of the indication of which sensor generated the temperature or pressure signal that differed by the predetermined amount.

The user may begin use by first effecting the storage of pressure and temperature signals within the memory. After, the user may then periodically utilize the present invention to detect any anomalies in size and temperature of the breasts which in turn provides an indication of a possible tumor or infection. As an option, a separate brassiere may be utilized to transmit gamma rays to the breast upon ascertaining the existence and location of a tumor.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A new and improved breast anomaly detection system comprising, in combination:

a brassiere including a pair of cups each having a rear opening with an arcuate upper edge, an arcuate outer side edge, a linear bottom edge, and an arcuate inner side edge, with the inner side edges of the rear openings of the cups stitchedly coupled by way of a generally triangular piece of fabric, the brassiere further including a back strap with ends coupled to the outer side edges of the rear openings of the cups and a pair of shoulder straps coupled between the back strap and the upper edges of the rear openings of the cups, whereby a female user may wear the brassiere such that each breast thereof resides within an associated one of the cups;

a pair of temperature sensors each coupled to an associated cup of the brassiere adjacent an interconnection of the upper edge and outer side edge thereof, each temperature sensor adapted to emit a temperature signal representative of a current temperature of the breast located within the associated cup;

a pair of strain gauges each coupled to an associated cup of the brassiere adjacent a central extent of the bottom edge thereof, each strain gauge adapted to emit a pressure signal representative of a current pressure that is exerted by the breast on the associated cup;

a multiplexer connected to each of the temperature sensors and strain gauges for allowing the transmission from an output thereof the temperature signals and pressure signals one at a time upon receipt of an activation signal;

an analog to digital converter connected to the output of the multiplexer for transforming the temperature signals and pressure signals from analog form to digital form;

memory means adapted to store and transmit a pair of temperature signals and pressure signals in digital form;

control circuitry connected between the multiplexer, analog to digital converter, and memory means for transmitting a continuous sequence of activation signals to the multiplexer and comparing the digital temperature signals and pressure signals received from the analog to digital converter with the temperature signals and pressure signals received from the memory means, respectively, upon the transmission of each activation signal, the control circuitry further adapted to transmit an alert signal upon at least one of the digital temperature signals and pressure signals received from the analog to digital converter differing from the respective temperature signals and pressure signals received from the memory means, respectively, by a predetermined amount whereby an anomaly in the breast can be detected; and printer means connected to the control circuitry for printing an alert upon the receipt of the alert signal.

2. A breast anomaly detection system as set forth in claim 1 wherein the brassiere has a rear opening with an arcuate upper edge, an arcuate outer side edge, a linear bottom edge, and an arcuate inner side edge, with the inner side edges of the rear openings of the cups stitchedly coupled by way of a generally triangular piece of fabric, the brassiere further including a back strap with ends coupled to the outer side edges of the rear openings of the cups and a pair of shoulder straps coupled between the back strap and the upper edges of the rear openings of the cups, whereby a female user may wear the brassiere such that each breast thereof resides within an associated one of the cups.

3. A breast anomaly detection system as set forth in claim 2 wherein the control means includes a multiplexer connected to each of the temperature sensors for allowing the transmission from an output thereof the temperature signals one at a time upon receipt of an activation signal;

an analog to digital converter connected to the output of the multiplexer for transforming the temperature signals from analog form to digital form;

memory means adapted to store and transmit a temperature signal in digital form;

control circuitry connected between the multiplexer, analog to digital converter, and memory means for transmitting a continuous sequence of activation signals to the multiplexer and comparing the digital temperature signals received from the analog to digital converter with the temperature signal received from the memory means, respectively, upon the transmission of each activation signal, the control circuitry further adapted to transmit an alert signal upon at least one of the digital temperature signals received from the analog to digital converter differing from the temperature from the memory by a predetermined amount; and printer means connected to the control circuitry for printing an alert upon the receipt of the alert signal.

4. A breast anomaly detection system comprising:

a brassiere including a pair of cups;

a pair of temperature sensors each coupled to an associated cup of the brassiere, each temperature sensor adapted to emit a temperature signal representative of a current temperature of the breast located within the associated cup;

control means for comparing the temperature signals with stored values and providing an alert upon the temperature signals differing from the stored values whereby an anomaly in the breast can be detected; and a pair of strain gauges each coupled to an associated cup of the brassiere, each strain gauge adapted to emit a pressure signal representative of a current pressure that is exerted by the breast on the associated cup, whereby the control means is further adapted for comparing the pressure signals with second stored values and providing an alert upon the pressure signals differing from the second stored values.

5. A breast anomaly detection system comprising:

a brassiere including a pair of cups;

a pair of strain gauges each coupled to an associated cup of the brassiere, each strain gauge adapted to emit a pressure signal representative of a current pressure that is exerted by the breast on the associated cup; and control means for comparing the pressure signals with stored values and providing an alert upon the pressure signals differing from the stored values whereby an anomaly in the breast can be detected.

6. A breast anomaly detection system as set forth in claim 5 wherein the control means includes a multiplexer connected to each of the temperature sensors for allowing the transmission from an output thereof the temperature signals one at a time upon receipt of an activation signal;

an analog to digital converter connected to the output of the multiplexer for transforming the temperature signals from analog form to digital form;

memory means adapted to store and transmit a temperature signal in digital form;

control circuitry connected between the multiplexer, analog to digital converter, and memory means for transmitting a continuous sequence of activation signals to the multiplexer and comparing the digital temperature signals received from the analog to digital converter with the temperature signal received from the memory means, respectively, upon the transmission of each activation signal, the control circuitry further adapted to transmit an alert signal upon at least one of the digital temperature signals received from the analog to digital converter differing from the temperature from the memory by a predetermined amount; and printer means connected to the control circuitry for printing an alert upon the receipt of the alert signal.

7. A breast anomaly detection system as set forth in claim 5 wherein the brassiere has a rear opening with an arcuate upper edge, an arcuate outer side edge, a linear bottom edge, and an arcuate inner side edge, with the inner side edges of the rear openings of the cups stitchedly coupled by way of a generally triangular piece of fabric, the brassiere further including a back strap with ends coupled to the outer side edges of the rear openings of the cups and a pair of shoulder straps coupled between the back strap and the upper edges of the rear openings of the cups, whereby a female user may wear the brassiere such that each breast thereof resides within an associated one of the cups.

\* \* \* \* \*

UNITED STATES PATENT AND TRADEMARK OFFICE
CERTIFICATE OF CORRECTION

PATENT NO. : 5,830,159
DATED : November 3, 1998
INVENTOR(S) : Henrietta Netta

It is certified that error appears in the above-indentified patent and that said Letters Patent is hereby corrected as shown below:

On the title page, item [76] inventor's address on
line 4, "246 Coal St., Wilkes- Barre, PA 18702" should read--
500 Schooley Ave. H-67, Exeter, PA 18643-1134--.

Signed and Sealed this

Tenth Day of August, 1999

Attest:

Q. TODD DICKINSON

Attesting Officer

Acting Commissioner of Patents and Trademarks